(12) United States Patent
Spranza, III

(10) Patent No.: US 6,884,245 B2
(45) Date of Patent: Apr. 26, 2005

(54) HARDWARE FOR CUTTING BONE CORES

(76) Inventor: Joseph John Spranza, III, 12493 Old Rough & Ready Hwy, Grass Valley, CA (US) 95945

( * ) Notice: Subject to any disclaimer, the term of this patent is extended or adjusted under 35 U.S.C. 154(b) by 219 days.

(21) Appl. No.: 10/127,142

(22) Filed: Apr. 22, 2002

(65) Prior Publication Data

US 2003/0199879 A1 Oct. 23, 2003

(51) Int. Cl.[7] ........................... A61B 17/14; A61B 17/16
(52) U.S. Cl. .............................. 606/79; 606/80; 606/53; 408/204
(58) Field of Search ................................ 408/204, 207, 408/211, 227, 703; 606/170, 179, 79–85

(56) References Cited

U.S. PATENT DOCUMENTS

| | | | | |
|---|---|---|---|---|
| 3,382,743 A | * | 5/1968 | Trevathan | .................. 408/204 |
| 3,609,056 A | * | 9/1971 | Hougen | ....................... 408/204 |
| 4,649,918 A | * | 3/1987 | Pegg et al. | .................... 606/79 |
| 5,697,935 A | * | 12/1997 | Moran et al. | ................ 606/104 |

* cited by examiner

*Primary Examiner*—Julian W. Woo
*Assistant Examiner*—Sarah Webb

(57) ABSTRACT

A surgical bone coring cutter is tubular in shape with the cutting end fabricated of a thicker section wall designed with both an inner and an outer cone. The double cone section causes the kerf to be wider than the wall thickness of the cutter shank, and the resulting clearance reduces friction and heat. Cutting element faces are at an essentially normal angle to the surface being cut and are supported by very long and relatively wide ramps of minimal relief angle. The ramps follow the cutting surfaces, carry off heat, and they prevent the cutter from digging in. The Cutter profile reduces tissue trauma and provides highly controlled advance of the cutter. The cutter is fabricated of several different materials; a hard material for sharpness and longevity of the cutting head and a resilient material for a shock resistant driving shank.

3 Claims, 6 Drawing Sheets

HARDWARE FOR CUTTING BONE CORES

BACKGROUND

1. Field of Invention

Figure 1:
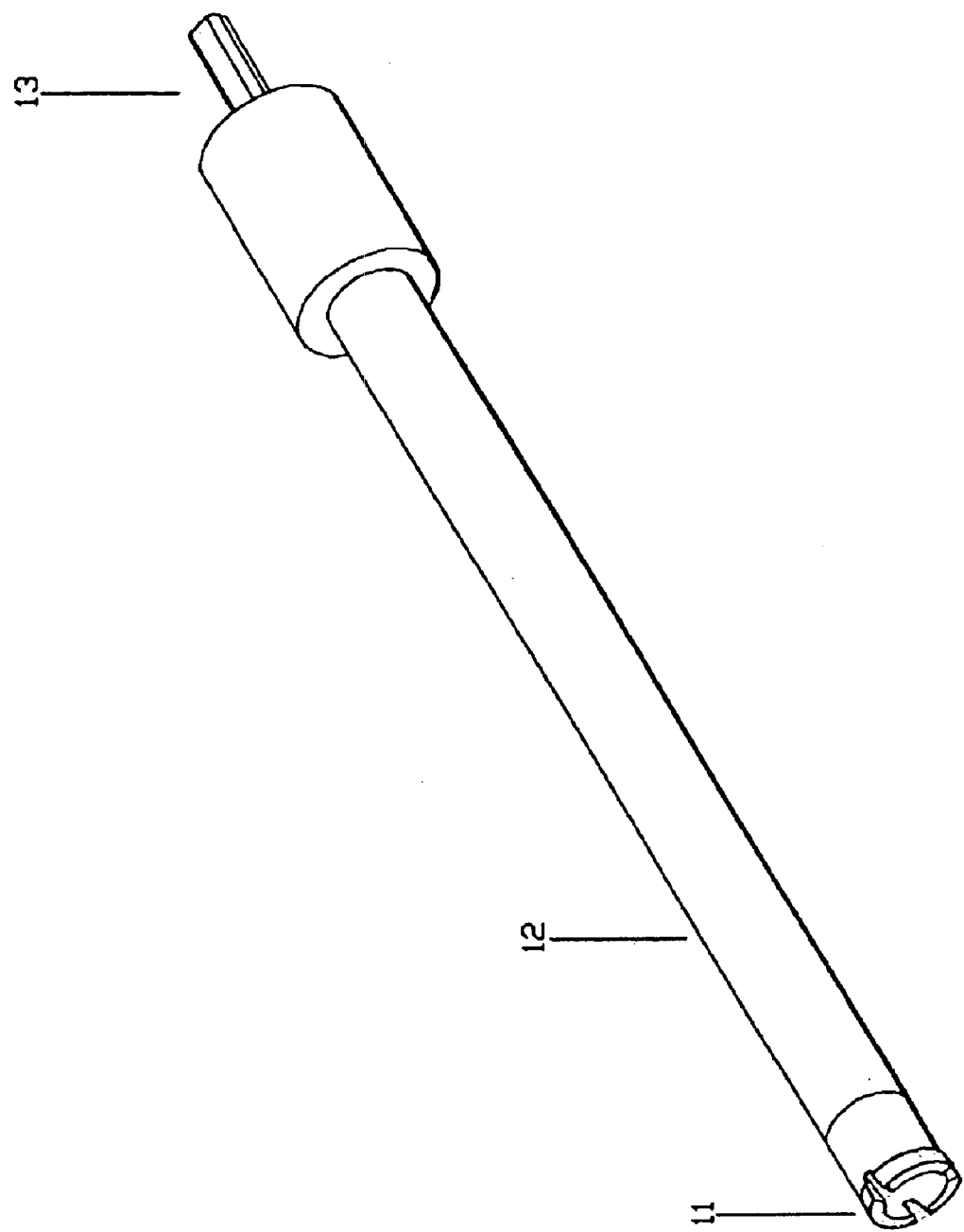

This invention relates to the surgical cutting of bone cores.

2. Description of Prior Art

The process of cutting cores from bone is a surgical procedure seen more frequently in recent years. Cores are cut and removed from bone when it is required to gain access to the inside of the bone such as the medullary canal or the inside of the skull. Access may be required to create a window for therapy. Another reason to cut a bone core is to obtain a bone specimen for diagnostic purposes. A further reason to cut a bone core is to harvest bone for grafting. Still another reason to core bone is to insert something into the bone, such as an item of hardware. The removed core is sometimes replaced after surgery, when it is used to close the bone (the core becomes a plug) after the procedure is completed. In some cases, the removed core is morselized and thereafter used as bone graft. The core, therefore, must not be damaged by heat and it should have relatively smooth cut surfaces. It is desirable in all cases to minimize invasion of soft tissue and reduce trauma to the core and to the surrounding bone. These criteria are very important. Former techniques and hardware employed in cutting cores from bone are known to cause trauma to the tissue. The hardware previously available caused damage by tearing both the soft and the bony tissue. These early coring cutters (also known as trephines) have significantly pointed teeth. An example of one such cutter was the Trephine for iliac crest bone graft cutting, marketed by Zimmer Medical, Inc. The teeth of some coring cutters had a positive rake angle; that is, the surface of a tooth was at less than 90 degrees to the surface being cut. The acute angle of attack caused the tooth to dig in to the tissue. Additionally, the clearance angle (that angle behind the tooth, in relation to the surface being cut) was very high, allowing too quick advancement of the coring cutter as it revolved. Because of such tooth geometry, previous coring cutters were also difficult to control. These pointed teeth tend to dig into and grab and tear tissue. The pointed teeth digging into the soft tissue and even the bony tissue grabbed and pulled the cutter into the bone. The hardware of this invention is designed to provide a controlled advance of the cutter as it is revolved. Such controlled cutter advance prevents 'digging in' of the cutter and promotes smooth, controlled cutting. Another disadvantage in the pointed cutting surfaces of earlier technology is that the teeth are prone to premature wear at the cutting edges, thus becoming dull after little use. When dull, the teeth do not cut cleanly; they tear, rather than cut, both soft and bony tissue. The Cutter of this invention is designed stay sharp longer and therefore to cut cleaner. In addition to the physical design, the material technology employed in the cutter of this invention enables the Cutter to achieve a sharper edge and then maintain a sharper cutting action. Another problem with former technology was that some damage to the bone was caused by the generation of excessive heat. The friction created by dull cutting edges causes heating of the bone; both the parent bone and the cored bone. Such heating leads to osteonecrosis (bone death). Therefore, using hardware and methods available hereto-fore has resulted in the harvest of bone cores having impaired viability. Because of the materials from which this cutter is made, it demonstrably cuts more cleanly for an extended period of time with minimum friction. Reduced friction means reduced heating of the parent bone and of the core, resulting in more viable bone plugs. Further, with previous bone coring cutters, there was excessive friction on the bone by the cutter body, leading to increased temperatures. This friction lead to heating. The hardware of this invention is designed to reduce heating by reducing friction between the body of the Cutter and bone. The Cutter of this invention has both internal diameter and external diameter relief to allow freedom from friction between the shank and the bone. Additionally, by design, the Cutter of this invention conducts heat away from the cutting areas. Metal is a better heat conductor than is bone. The wide, long ramps behind the cutter faces of this Cutter conduct more heat than the slim pointed cutting faces of former cutters. Therefore the cutting sites remain cooler. Because of the design, the Cutter of this invention advances with easily controlled action without digging and tearing. This Cutter is sharper when new and stays sharper for longer periods of time. The Cutter of this invention creates less heat, and conducts heat away from the bone than did former cutters. The advantages of this Cutter result in cleaner, straighter holes and cleaner, cooler, more viable bone and bone cores.

OBJECTS AND ADVANTAGES

Accordingly, several objects and advantages of the present invention are:

(a) to provide a bone coring cutter that by design will provide a very controlled cutting and advancing action, (b) to provide a bone coring cutter that is sharper when new and that remains sharper during use, (c) to provide a bone coring cutter and system that produces a cleanly cut, viable bone plug, (d) to provide a bone coring cutter that has both internal diameter and external diameter clearance between the cutter body and the bone, (e) to provide a bone coring cutter that generates less heat than former coring cutters, (f) to provide a bone coring cutter that carries heat from the cutting zone away from the bone core, (g) to provide a bone coring cutter that cuts cleaner, cooler, straighter holes with less trauma from heating and tearing.

Further objects and advantages are to provide a bone coring system that may be used quickly and easily. Still further objects and advantages will become apparent from a consideration of the ensuing description and drawings.

DRAWINGS FIGURES

In the drawings, closely related figures have the same number but different alphabetic suffixes.

FIG. 1 The bone core Cutter assembly

Figure 2:
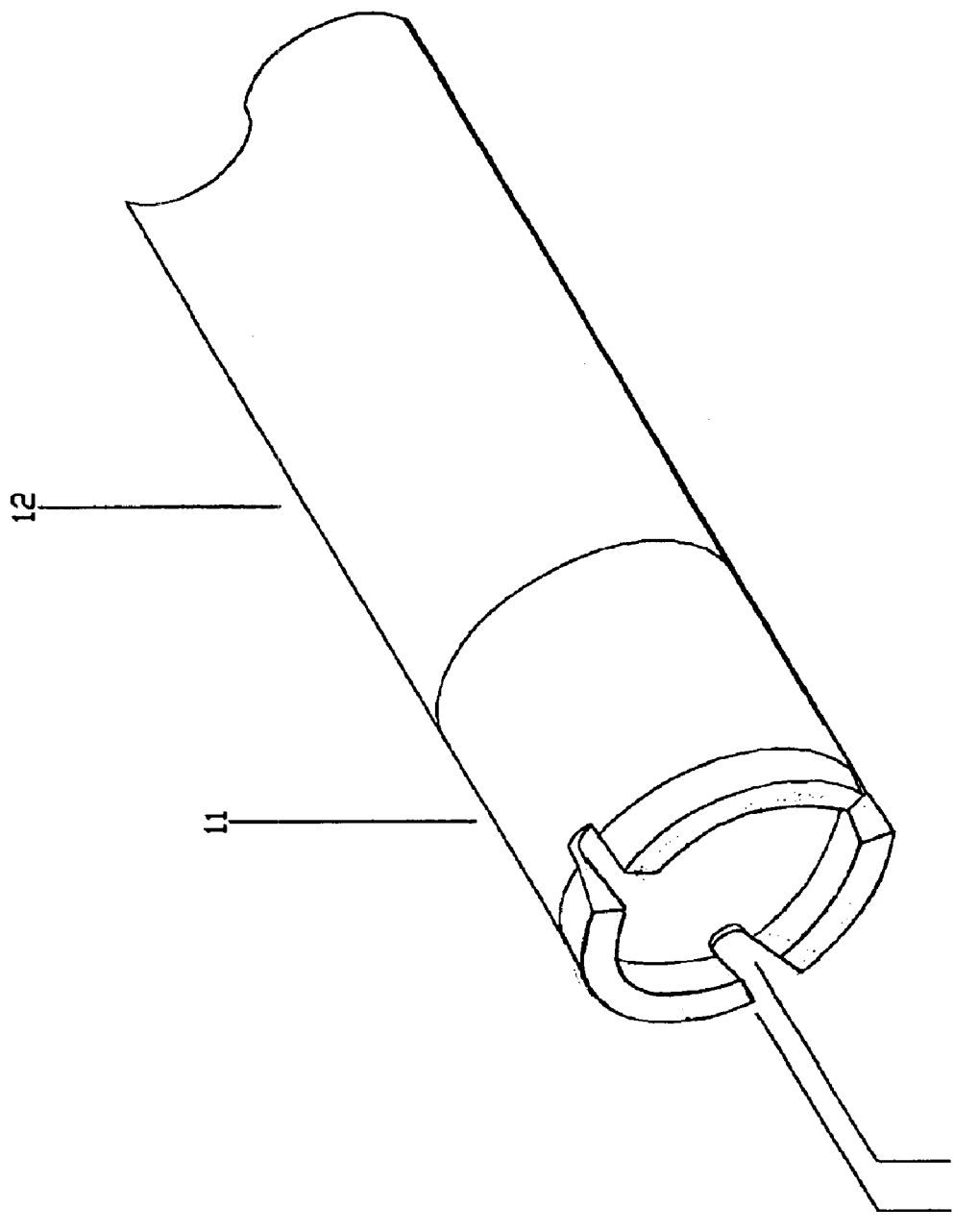

FIG. 2 The bone core Cutter head

Figure 3:
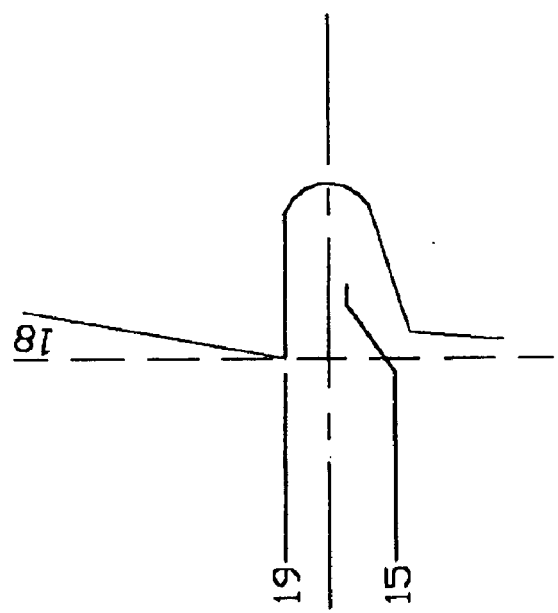
Figure 3:
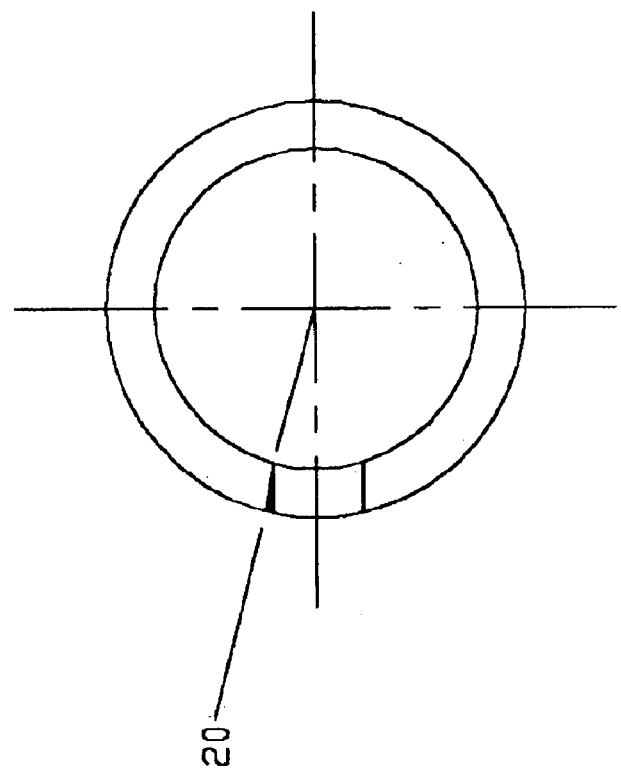

FIG. 3 Details of the cutting surfaces

Figure 4:
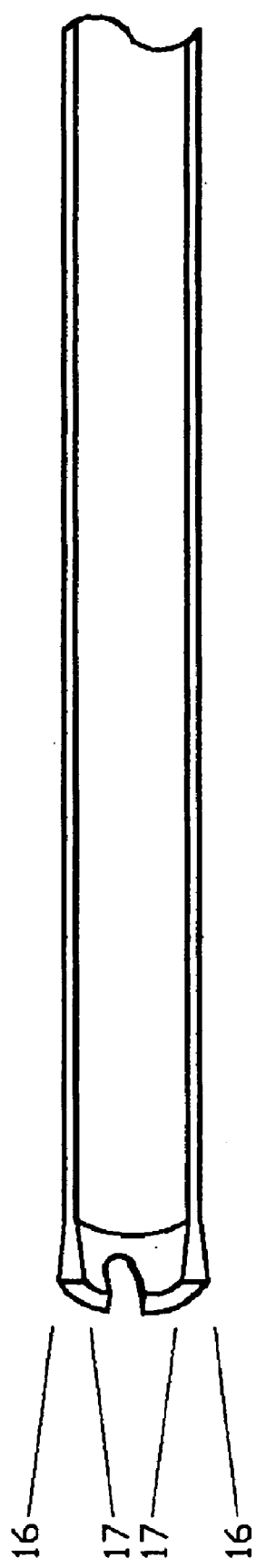

FIG. 4 Cutter assembly Sectional View

Figure 5:
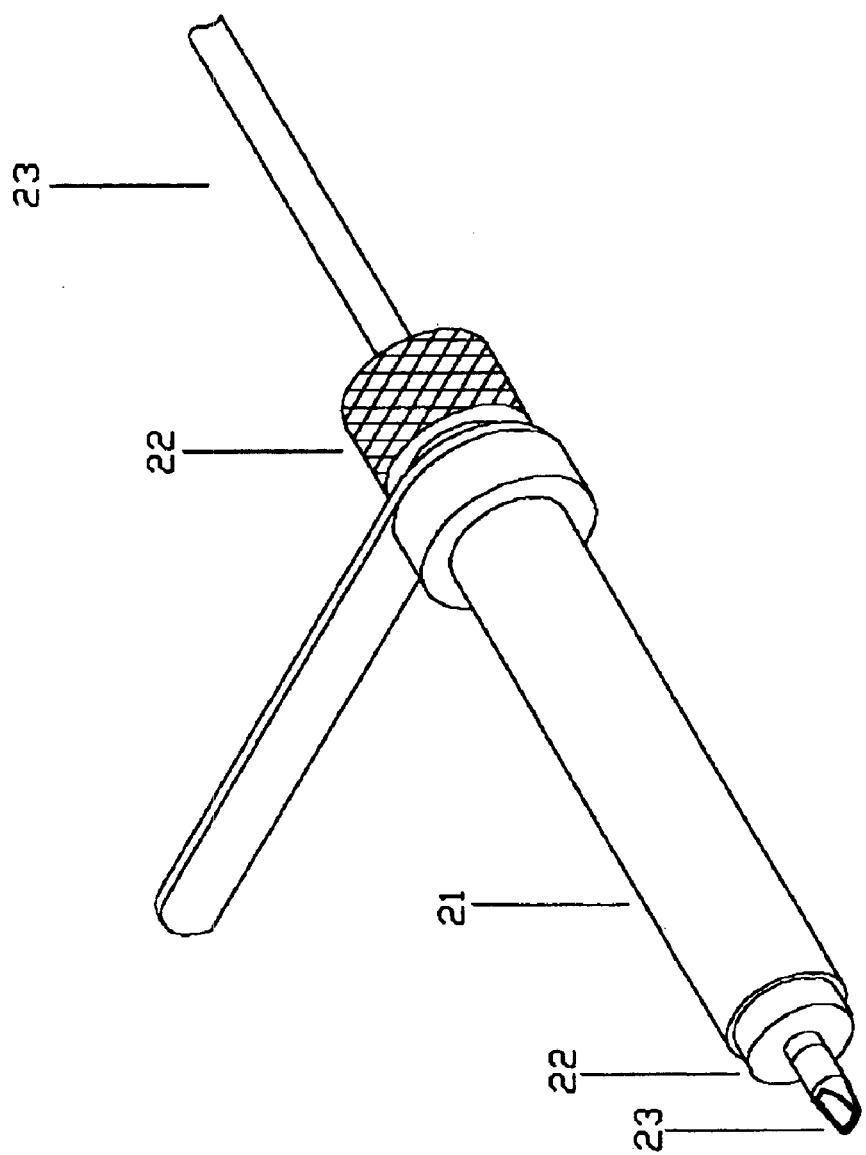

FIG. 5 Tissue Protector with Obturator in-situ

Figure 6:
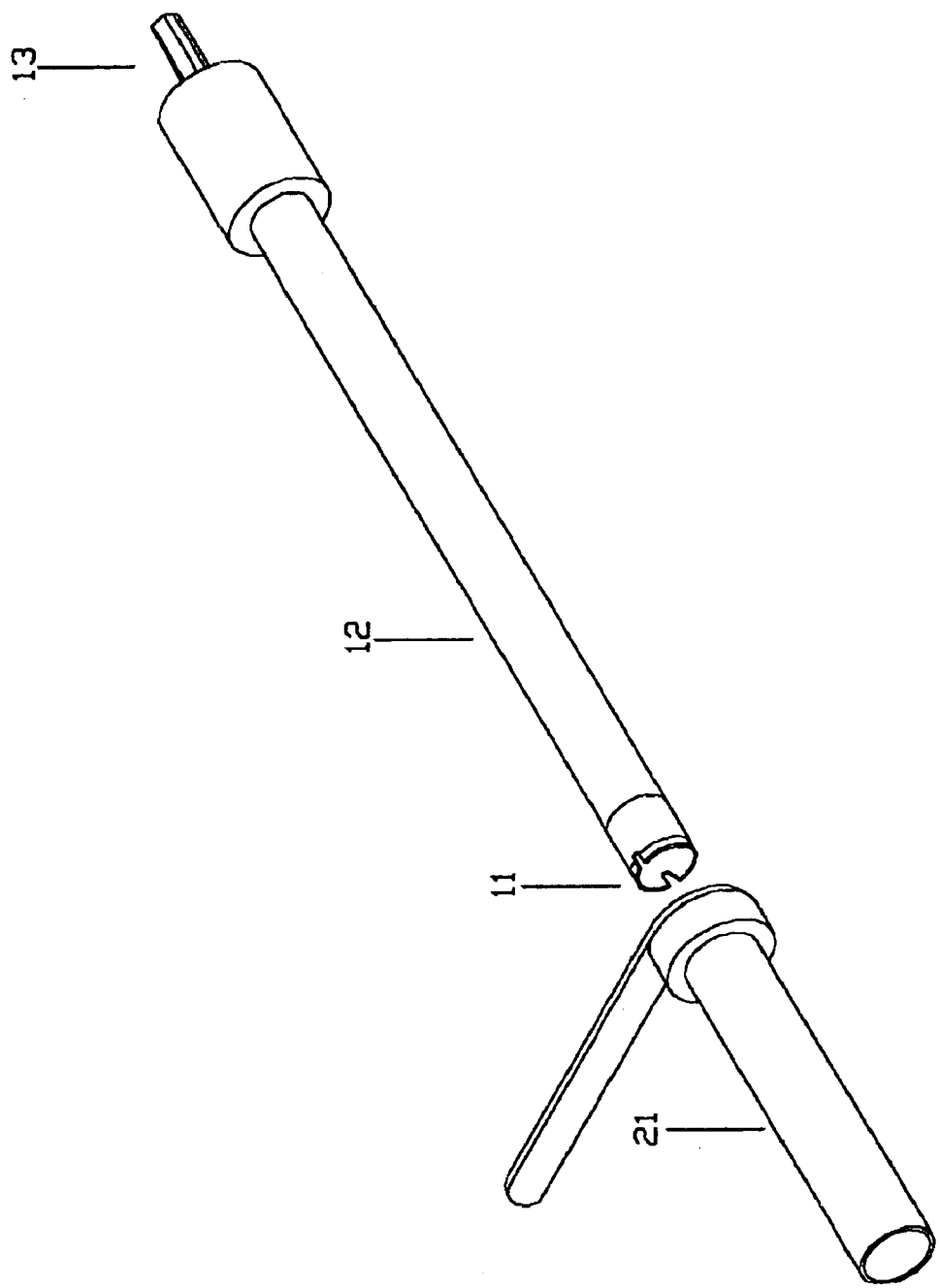

FIG. 6 Cutter assembly aligned for insertion into Tissue Protector

NUMERALS IN DRAWINGS

11 Cutting head
12 Shank
13 Drive Tang (connective means)

14 Cutting edge
15 Chip space
16 Outer kerf angle
17 Inner kerf angle
18 Tooth clearance relief angle
19 Linear rake angle
20 Radial rake angle
21 Tissue Protector
22 Obturator/Stabilizer
23 Guide Wire

SUMMARY

The hardware of the present invention is a tubular Cutter for coring bone. The Cutting head has both an inner and an outer cone so that the resulting kerf provides adequate clearance for bone-to-shank relief to reduce friction, and therefore to reduce power requirements and heat generation. The Cutting head has a cutting edge linear rake angle that is substantially small, to reduce "digging in" and tearing tissue. The Cutting head has a substantially small relief angle that limits the depth of cut per revolution, therefore giving a more controlled advance of the Cutter. Therefore, the Cutter advance is very smooth and controlled. The Cutting head has a zero radial relief angle such that the chips flow to both the inner and outer diameter. The cutter is designed and fabricated of multiple materials; the cutting head of harder material, to be sharper when new and remain sharper over long periods of use, and the shank of a resilient material to provide a shock resistant torque tube. The combination of cool cutting, sharp cutting without tearing, and controlled advance in cutting results in a cooler, smoother and more viable bone core, with less trauma to surrounding parent bone.

Description—FIGS. 1 through 6

A typical embodiment of the bone coring Cutter system of the present invention is illustrated in FIGS. 1 and 2. FIG. 1 shows an isometric view of a complete Cutter assembly. The Cutter assembly consists of a cutting head #11, a shank #12, and a drive (adapter) tang #13. FIG. 2 shows the cutting head #11 in greater detail. The cutting end "cutting head", shown in FIG. 2 of the Cutter assembly, is of a different material from that of the tube (shank). The different materials are selected to enhance cutting sharpness and durability of the cutting teeth, and shock resistance of the shank. The chip space #15 is adequate for the small chip fragments (as a byproduct of the cutting action of this cutter) produced by this cutter. FIG. 4 shows a cross sectional view of the cutter head. For descriptive clarity, the angles are exaggerated. Notice that the cutting end is cone shaped both on the outer diameter and on the inner diameter. The cones have angles subtended at opposite ends of the long axis. FIG. 4 shows extension lines of the cones: #16 being extension lines of the outer cone and #17 being extension lines of the inner cone. This double cone shaping results in cutting surfaces that are "dovetail" in cross section. The cutting end of the dovetail is greater in width than the root end, and this greater width of the tooth end results in cutting a kerf wider than the root of the cutting element. The slightly wider kerf provides clearance for and precludes friction between the thinner-walled tubular body and shank of the Cutter and the walls of the hole and of the core. In FIG. 3, the cutting tooth face shown is at a nominal 90-degree (zero angle of attack) to the material being cut. This is the linear rake angle #19. Because the cutting angle is normal to the surface being cut, the cutting element does not dig in and tear tissue. Supporting and following the cutting face is a very long and relatively wide ramp minimal slope; the relief angle behind the cutting face. This low relief angle allows only a very light (thin) cut into the bone, providing for a well controlled cutter advance. The long, low relief angle and the wider surface also serve to conduct heat away from the surface being cut. Note also that the tooth face is at a zero angle to the radial ray, the line that rays out from the centerline (long axis) of the Cutter. This is the radial rake angle #20. The zero radial rake angle results in chips flowing equally to the inside and outside of the cutter. Such chip flow results in cleaner hole walls and cleaner bone cores.

Operation—FIGS. 5, 6

The manner of using the bone coring cutter of this invention is as described below. Select a drill motor that will be used to rotate the Cutter assembly. It is possible, as an alternative to power rotation, to hand rotate the Cutter. The cutting rotation should be clockwise and should be limited to relatively low rotational speeds. (Rotational speeds on the order of 50 to 100 revolutions per minute are adequate.) Using fluoroscopic visualization, drive a guide wire into the bone from where the core specimen will be cut. The guide wire should be driven into the bone about a centimeter deep and at vector angle pointing to the desired spot to be cut. Make a short incision in the skin surrounding the guide wire, above where it is desired to take the core. Separate the overlying tissue by finger. Insert the Tissue Protector with Obturator, (FIG. 5) using some lateral manipulation to advance the cutter between tissue strands. Gently work the Tissue Protector #21 with Obturator #22 over the guide wire #23, down to the bone (See FIG. 5). Remove the Obturator by pulling it straight out of the Tissue Protector. Remove the guide wire. Insert the Cutter assembly, (FIG. 6) into the Tissue Protector, down to the bone. Hand rotate the Cutter Assembly to feel that it is cutting the periosteum and some of the cortical bone. Couple the drive motor coupling to the drive tang (FIG. 1 #13) of the Cutter assembly. Direct the Cutter at the correct angle so that the Cutter will cut and advance to the correct location. Rotate the Cutter with the drill motor and advance the Cutter with light pressure into the bone, observing the correct progress with the aid of fluoroscopic visualization. Advance the Cutter to the desired depth. At the appropriate depth, de-couple the drill motor. Withdraw the Cutter assembly with the bone core inside.

After performing the required surgery in the medullary canal it is possible to replace the bone core into the original position. Close the incision by using standard surgical procedure.

CONCLUSIONS, RAMIFICATIONS, AND SCOPE

Accordingly, the reader will see that the bone coring hardware of this invention enables a surgeon to easily and quickly cut a bone core from parent bone with minimal damage to the core and to the surrounding soft tissue and bone. This hardware provides minimal invasion because it may be used as a percutaneous procedure, through soft tissue with the aid of a Tissue Protector. The core cut by this hardware may be used as a plug to close the bone when the procedure is completed.

The hardware of this invention is superior to previous core cutters because:

It develops little heat

It conducts heat away from the bone

It does not dig in and tear soft tissue and bone

It cuts cleanly

It stays sharper, longer

It is easy to control

The core as cut is viable and may be re-inserted as a plug

The core may be used as bone graft

Although the description above contains many specificities, these should not be construed as limiting the scope of the invention but as merely providing illustrations of some of the presently preferred embodiments of this invention. For example, different materials may be used. Different materials may be used in combination, or, one material only may be used. The number of teeth may vary from one through multiples of two or three. Additionally, the relief angle may be changed to provide a cutter more suitable for other materials. To facilitate the cutting of materials other than bone, the linear rake angle may be varied. To meet the requirements of different materials and end uses, the radial rake angle may be varied. The cutting face surface may be curved in one or more dimensions. Yet additionally, the radial rake angle may be changed to move the cuttings (chips) either to the center of the Cutter or to the outside of the Cutter. Further, the cone angles may be varied from nearly zero to a substantial angle. Yet further, the inner cone may have a different angle from the outer cone.

Thus, the scope of the invention should be determined by the appended claims and their legal equivalents, rather than by the examples given.

I claim:

1. A bone coring cutter comprising
   a. a cutting head, the end plane of which is the broadest base of a tubular double cone with the outer cone converging to intersect the outer diameter of a right circular cylinder and the inner cone diverging to intersect the inner diameter of said right circular cylinder such that said cutting head has an outer diameter cone, the angle of which is subtended within the cutter body and an inner diameter cone, the angle of which is subtended outside said cutter body so that in cross section said tubular double cone is a dovetail and wherein said cutting head tubular double cone is cut away in multiple places to effect peaks, each cut away portion leaving a profile described as proceeding substantially linearly parallel to the linear axis into the body of said cutting head and thence along a somewhat circular path returning toward said end plane and then along a substantially straight line angled relative to said linear axis to a point of intersection with a primarily sloping line running toward said cutting head end plane and intersecting with the axially parallel line of the next cut away portion, the profile repeated for each cutting surface, and wherein said cutting head is affixed to
   b. a shank tube which is a right circular cylindrical tube of substantial length affixed at the opposite end, to
   b. a connector end that has a coupling means for attachment to a rotation source, whereby said coring cutter cuts a kerf of adequate dimension to reduce friction and heat, conducts heat away from the bone, cuts cleanly without digging in and tearing tissue and has a limited advance per revolution.

2. The cutter of claim 1, wherein
   a. said cutter head is made of a material which can be hardened
   b. said shank is made of a material which will withstand shock without fracturing, and
   c. said cutter and shank are bonded together as an assembly, whereby said cutter of claim 1 may be finely sharpened and stay sharp through many uses.

3. The cutter of claim 2, wherein
   a. said cut-away portions number three,
   b. have a zero linear rake
   c. have a zero radial rake
   d. have a substantially low relief angle.

* * * * *